United States Patent [19]

Merritt et al.

[11] Patent Number: 5,344,431
[45] Date of Patent: Sep. 6, 1994

[54] METHOD AND APPARATUS FOR DETERMINATION OF END-OF-SERVICE FOR IMPLANTABLE DEVICES

[75] Inventors: Donald R. Merritt, Brooklyn Center; William G. Howard, St. Paul; Paul M. Skarstad; Douglas J. Weiss, both of Plymouth; Paul B. Wyborny, Coon Rapids; Glenn M. Roline, Anoka; Lucy M. Nichols, Maple Grove; David L. Thompson, Fridley, all of Minn.

[73] Assignee: Medtronic, Inc., Minneapolis, Minn.

[21] Appl. No.: 944,872

[22] Filed: Sep. 14, 1992

Related U.S. Application Data

[63] Continuation-in-part of Ser. No. 896,641, Jun. 10, 1992, which is a continuation-in-part of Ser. No. 765,475, Sep. 25, 1991, Pat. No. 5,127,404, which is a continuation of Ser. No. 468,407, Jan. 22, 1990, abandoned.

[51] Int. Cl.$^5$ .............................................. A61N 1/00
[52] U.S. Cl. .................................... 607/29; 607/32; 128/903
[58] Field of Search ....... 128/419 P, 419 PG, 419 PS, 128/419 PT, 903; 607/9, 33, 34, 27, 29; 429/224

[56] References Cited

U.S. PATENT DOCUMENTS

| | | | |
|---|---|---|---|
| 4,026,305 | 5/1977 | Brownlee et al. | 128/419 PT |
| 4,231,027 | 10/1980 | Mann . | |
| 4,327,166 | 4/1982 | Leger . | |
| 4,399,202 | 8/1983 | Ikeda . | |
| 4,448,864 | 5/1984 | Broussely . | |
| 4,550,370 | 10/1985 | Baker . | |
| 4,556,063 | 12/1985 | Thompson . | |
| 4,589,112 | 5/1986 | Karim | 371/37 |
| 4,606,350 | 8/1986 | Frost | 128/419 PG |
| 5,137,020 | 8/1992 | Wayne et al. | 128/419 PS |

*Primary Examiner*—Lee S. Cohen
*Assistant Examiner*—Marianne Parker
*Attorney, Agent, or Firm*—Daniel W. Latham; Harold R. Patton

[57] ABSTRACT

A method and apparatus for determination of battery end-of-service in a medical device in which the medical device comprises a cathode limited electrochemical cell having an active metal anode and a manganese dioxide cathode and means for digital telemetry of cell voltage. The sloped, well defined voltage curve of such a cell during cell discharge combined with precise information available through digital telemetry allows for improved determination of battery end-of-service for the medical device.

10 Claims, 12 Drawing Sheets

METHOD AND APPARATUS FOR DETERMINATION OF END-OF-SERVICE FOR IMPLANTABLE DEVICES

This application is a continuation-in-part of U.S. Ser. No. 07/896,641, filed Jun. 10, 1992, which is a continuation-in-part of U.S. Ser. No. 07/765,475, filed Sep. 25, 1991, now issued as U.S. Pat. No. 5,127,404, which is a continuation of U.S. Ser. No. 07/468,407, filed Jan. 22, 1990, now abandoned.

BACKGROUND OF THE INVENTION

The present invention generally relates to implantable medical devices, and to telemetry schemes for percutaneously transmitting end of battery service data from the implantable medical device and even more particularly to telemetry relating to manganese dioxide electrochemical cells.

In implantable medical devices, the desirability to transfer more data at higher speeds has resulted in the percutaneous transmission of data using a radio frequency carrier. The data to be transmitted are of two basic types, namely, analog and digital. The analog information can include, for example, battery voltage, intracardiac electrocardiogram, sensor signals, output amplitude, output energy, output current, and lead impedance. The digital information can include, for example, statistics on performance, markers, current values of programmable parameters, implant data, and patient and unit identifiers.

The earliest RF telemetry systems transmitted analog and digital information in separate formats, resulting in inefficient utilization of the available power/bandwidth. Also, these modulation schemes tended to be less than satisfactory in terms of battery consumption, and did not lend themselves to simultaneously transmission of differing data types.

Many types of RF telemetry systems are known to be used in connection with implantable medical devices, such as cardiac pacemakers. An example of a pulse interval modulation telemetry system used for transmitting analog and digital data, individually and serially, from an implanted pacemaker to a remote programmer is disclosed in U.S. Pat. No. 4,556,063 issued to Thompson et al., herein incorporated by reference. An example of a modern pacemaker programmer for use with programmable cardiac pacemakers having RF telemetric capabilities is disclosed in U.S. Pat. No. 4,550,370 issued to Baker, herein incorporated by reference. An example of voltage telemetry is disclosed in U.S. Pat. No. 4,231,027 issued to Mann et al., herein incorporated by reference. However, the telemetry format which is used under these systems, as well as other prior telemetry systems, have not been entirely adequate.

In particular, it has been noted that certain electrochemical cells utilized in implantable medical devices have changes in voltage that are indicators of impending end-of-service for the cell. However, even when such voltage changes are highly predictable for a particular cells, the telemetry system has been inadequate to give an accurate voltage to reliably predict end-of-service for the cell.

In implantable medical devices which have high current components such as pacemakers with oxygen sensors there is a need for electrochemical cells with a relatively high rate of discharge. This rate of discharge can be provided by cells using an active metal anode and manganese dioxide as the cathode material. However, when manganese dioxide has been used as a cathode material in an active metal anode electrochemical cell it has typically been an anode-limited cell. That is, that a stoichiometric excess of cathode material has been present in the cell so that at the end-of-service for the cell, the anode material is substantially consumed. This produces a cell with a very flat discharge voltage curve. In U.S. Pat. No. 4,399,202 to Ikeda et al., it has been recognized that the slope of the discharge voltage curve at end-of-service can be increased by increasing the relative amount of manganese dioxide in the cell.

However, such a flat discharge voltage curve with a steep slope at end-of-service is not desirable for use in critical implantable medical devices since it could arrive unexpectedly at its end-of-service with adverse consequences for the patient. In fact, it would be desirable in such a cell to provide a highly accurate determination of end-of-service well in advance of arrival of its end-of-service.

SUMMARY OF THE INVENTION

We have discovered a method and apparatus for highly accurate determination of end-of-service for electrochemical cells with manganese dioxide as a cathode material in implantable medical devices. The cell is cathode-limited to provide a highly reproducible voltage curve and the voltage is percutaneously transmitted from the implantable medical device in a digital format.

The cell voltage has been found to drop in a highly predictable fashion for cathode limited manganese dioxide electrochemical cells as they approach end-of-service. This is directly related to the consumption of cathode material rather than the increase of cell impedance as in the case of lithium/iodine cells.

Cell voltage is therefore a highly reliable indicator of remaining service life for the cell and can be very useful in a clinical setting provided that the voltage information can be transmitted with a high degree of accuracy. This can be accomplished by digital data transmission.

The voltage data to be sent is initially analog but it is transmitted as digital information. The RF carrier can be pulse position modulated to conserve battery energy. In this manner, only a short burst of the carrier, e.g., one cycle, is actually needed to transmit a given unit of data. The time position of that burst relative to a synchronizing standard can determine the value of the data unit transmitted.

To accomplish this pulse position modulation, a frame of about 2 milliseconds is defined. Within this frame are positioned a synchronizing burst, a frame identifier burst, and one or more data bursts. The synchronizing burst is positioned at a fixed position in the frame. The frame identifier and data are variables, such that the corresponding bursts occur within a range of time within the frame. The range in which a burst is found defines the nature or type of the variable. The position in the range defines the value of the variable.

Transmitting the analog voltage data in digital form in this manner provides enhanced noise immunity and accuracy.

DETAILED DESCRIPTION OF THE INVENTION

The present invention is disclosed in detail for an implantable cardiac pacer, which may be programmable and which will therefore include bi-directional communication of data in addition to the digital transmission of voltage data according to the present invention. However, those of skill in the art will be readily able to adapt the teachings found herein to other implantable medical devices.

Figure 1:
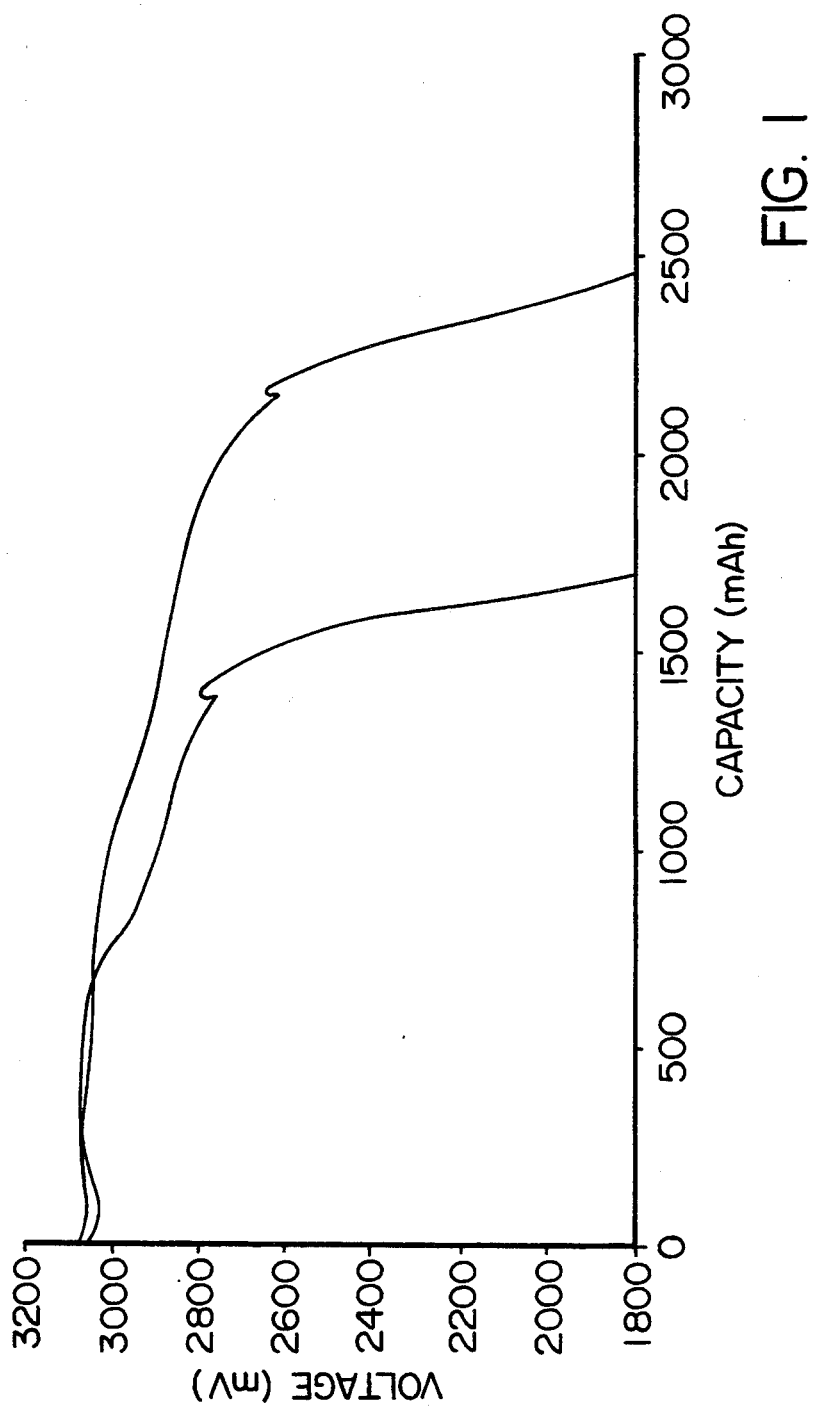
FIG. 1 shows discharge curves for two electrochemical cells of differing cathode capacities (2.50 ah and 1.75 ah) made according to the present invention in which voltage is plotted against capacity.
Figure 2:
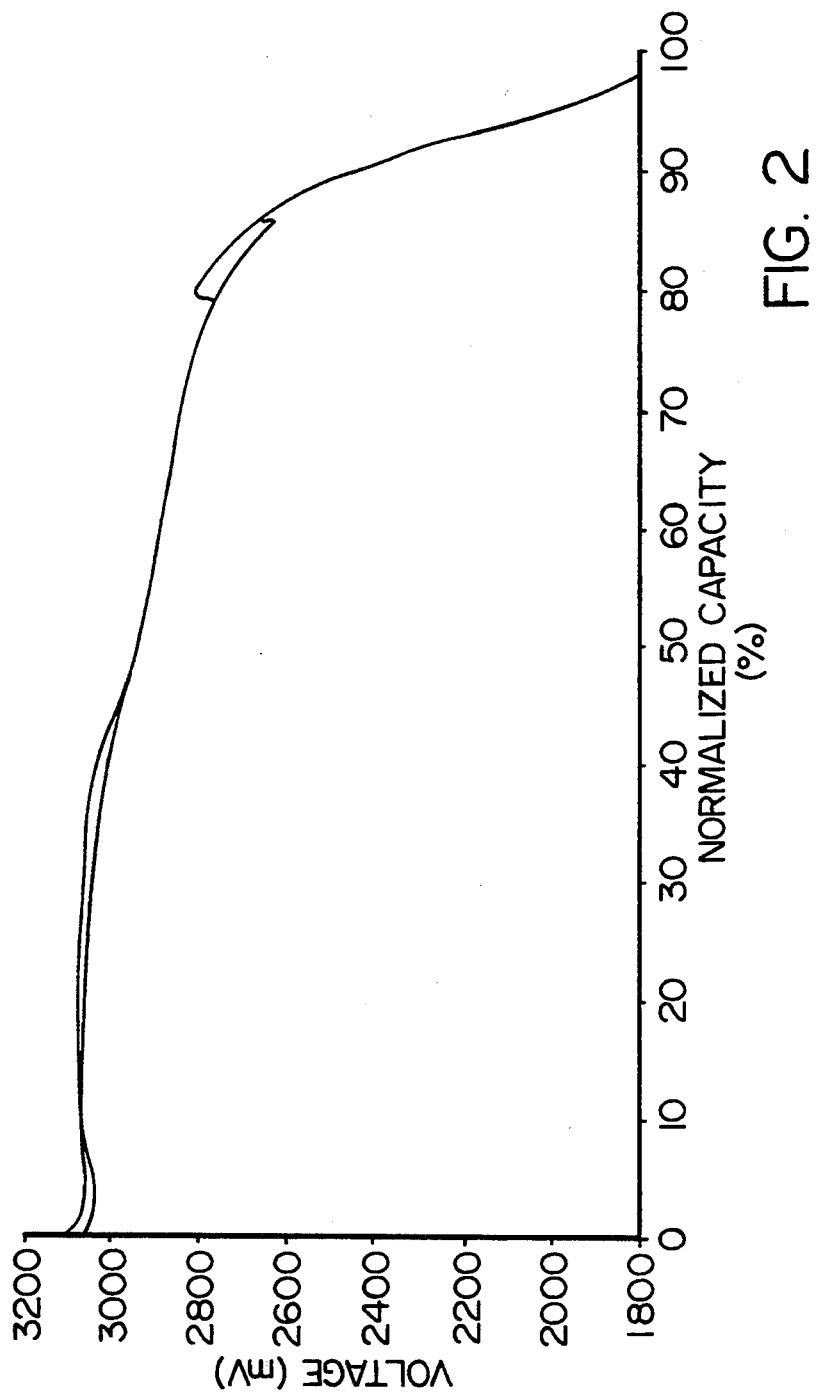
FIG. 2 shows discharge curves for the electrochemical cells of FIG. 1 with voltage plotted against normalized capacity.

The electrochemical cell of the present invention provides a discharge curve at end-of-service substantially as shown in FIG. 1 and FIG. 2. It will be noted that a although the cells have different cathode capacities, their normalized discharge curves as shown in FIG. 2 are virtually identical. Therefore, the voltage as an indication of end-of-service is independent of the amount of cathode material in the cell and can therefore be a highly reliable indicator of the state of discharge for any cathode-limited $MnO_2$ cell. It should also be noted that the discontinuities shown in the curves for FIG. 1 and FIG. 2 are only the result of change in the discharge rate from a higher rate to a lower rate during the test protocol.

The electrochemical cell includes an active metal anode such as lithium, sodium, potassium, calcium and alloys thereof; manganese dioxide as a cathode material; and an organic electrolyte including an organic solvent and a ionizing solute. The organic solvent can be, for example, 3-methyl-2-oxazolidone, sulfolane, tetrahydrofuran, methyl-substituted tetrahydrofuran, 1,3-dioxolane, propylene carbonate (PC), ethylene carbonate, gamma-butyrolactone, ethylene glycol sulfite, dimethylsulfite, dimethyl sulfoxide or mixtures thereof and also, for example, low viscosity cosolvents such as tetrahydrofuran (THF), methyl-substituted tetrahydrofuran (Met-THF), dioxolane (DIOX), dimethoxyethane (DME), dimethyl isoxazole (DMI), diethyl carbonate (DEC), ethylene glycol sulfite (EGS), dioxane, dimethyl sulfite (DMS) or the like. The ionizing solute can be a simple or double salt or mixtures thereof, for example, $LiCF_3SO_3$, $LiBF_4$, $LiAsF_6$, $LiPF_6$ and $LiClO_4$ which will produce an ionically conductive solution when dissolved in one or more solvents.

The relative proportions of anode material to cathode material are adjusted to make the cell cathode limited. That is, there is a stoichiometric excess of anode material so that when the cell reaches end-of-service the $MnO_2$ cathode material will be substantially exhausted while reactive anode material will still be available. This assumes a reaction involving the transfer of one electron per mole of $MnO_2$. For example, with a lithium anode, an appropriate capacity ratio of anode material to cathode material might be in the range of about 1.0 to about 1.5 while the ratio is preferably in the range of about 1.0 to about 1.2.

For example, in a preferred embodiment, cells can be constructed with 6.60 grams of a cathode mix of 91.8% manganese dioxide, 5.0% Shawinigan carbon, and 3.2% PTFE; an electrolyte of 1.0M $LiClO_4$ in 60 vol % PC/40 vol % diglyme; a two piece lithium anode weighing 0.51 grams; and a Celgard 4560 separator between anode and cathode. The manganese dioxide is first pretreated at 350° C. for 4–5 hours under air. The PTFE is then dispersed in water with a surfactant and mixed with the manganese dioxide and carbon. The resulting mixture is then vacuum baked at 275° C. for 16 hours under vacuum. The dry mix is then ground in a ball mill and pressed in a die into the desired shape for the cathode. The resulting cathodes are vacuum baked at 275° C. overnight and assembled and hermetically sealed into a welded stainless steel case of conventional design.

Figure 3:
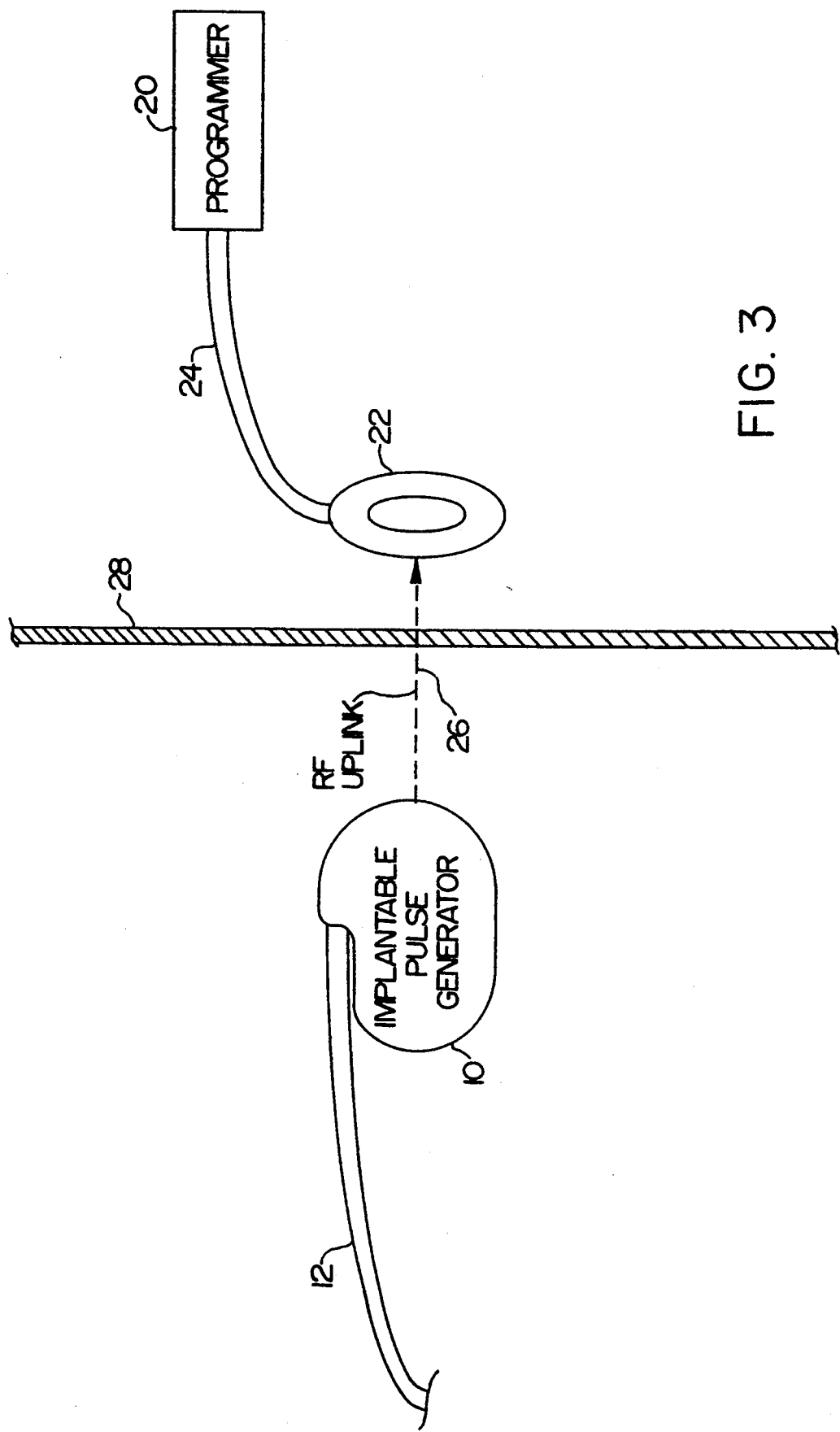
FIG. 3 is a simplified schematic view of an implantable medical device employing an electrochemical cell and digital RF telemetry according to the present invention.

FIG. 3 is a simplified schematic diagram of the telemetry system of the present invention as employed in a cardiac pacing system. An implantable pulse generator 10 is implanted in the patient under the outer skin barrier 28. Implantable pulse generator 10 is electrically coupled to the heart of the patient using at least one cardiac pacing lead 12 in a manner known in the art. Percutaneous telemetry data is transmitted from implantable pulse generator 10 by an RF uplink 26 to a receiving antenna 22, which is coupled to a programmer 20 via a cable 24. Receiving antenna 22 also contains a magnet which activates a reed switch in implantable pulse generator 10 as a safety feature, as taught in U.S. Pat. No. 4,006,086 issued to Alferness et al., herein incorporated by reference. The telemetry data is demodulated and presented to the attending medical personnel by programmer 20.

Figure 4:
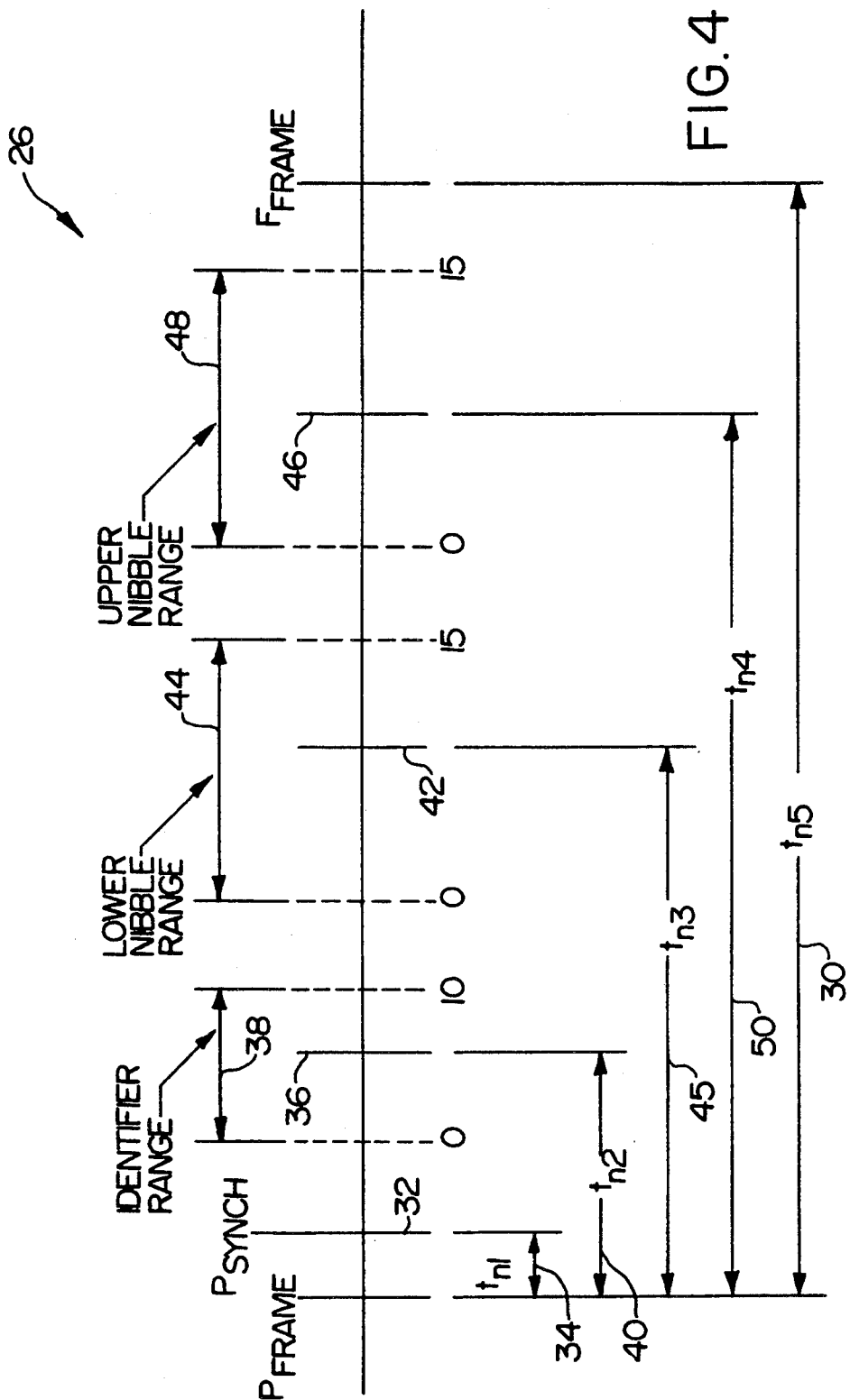
FIG. 4 is a conceptual view of one frame of a telemetry format according to the present invention.

FIG. 4 is a schematic diagram of the protocol of RF uplink 26. The uplink uses a damped 175 kilohertz RF carrier which is pulse position modulated as described in detail below. Shown at 30, the basic timing unit of the format is a frame, having a duration of $t_{n5}$. It will be understood by those skilled in the art, however, that the present invention can be practiced using fixed-length frames having periods of shorter or longer duration. In the preferred embodiment, the main timing source of implantable pulse generator 10 comprises a standard 32.768 kilohertz crystal clock which provides a basic clock cycle of 30.52 microseconds. Thus, a frame comprised of 64 clock cycles and extending over a fixed time interval of 1.953125 milliseconds is a convenient frame period, since such frame period is a binary multiple of the basic clock cycle.

A synchronizing signal is positioned within a first fixed range of each frame 30. This signal comprises a synchronizing RF pulse 32 which is located at a time $t_{n1}$ within frame 30. To properly function as a synchronizing pulse, it must be located at a fixed point within the first fixed range of frame 30, as shown at 34.

A four-bit frame identifier code is positioned within a second fixed range of each frame 30, such second fixed range comprising an identifier range 38. Identifier range 38 uses a total of ten basic clock cycles as shown, permitting 11 unique values of the four-bit nibble to be specified. This identifier code comprises an identifier RF pulse 36 which is pulse position modulated within the identifier range 38. The position of identifier pulse 36 within identifier range 38 identifies the nature or type of data found within each frame 30 which is being transmitted, such as battery voltage, peak sense, peak pressure, sense threshold and other, as described in further detail below. Shown at 40, time interval $t_{n2}$ thus uniquely represents the value of identifier pulse 36, which value in turn identifies the data type being transmitted within frame 30.

Each frame 30 transfers one eight-bit byte of data along with the identifier code. This data is divided into two portions comprised of four bits of data each. A first portion of this data, namely the four least significant bits of the data byte, is positioned within a third fixed range of frame 30, such third fixed range comprising a lower nibble range 44. A second portion of this data, namely the four most significant bits of the data byte, is positioned within a fourth fixed range of frame 30, such fourth fixed range comprising an upper nibble range 48.

A lower nibble pulse 42 is pulse position modulated within lower nibble range 44, such that its value is uniquely identified by its location, such as at a time $t_{n3}$ shown at 45. An upper nibble pulse 46 is also pulse position modulated within upper nibble range 48, such that its value is uniquely identified by its location, such as at a time $t_{n4}$ shown at 50. Lower nibble range 44 and upper nibble range 48 each comprise fifteen basic clock cycles, permitting each of the sixteen unique values of the four-bit nibble to be specified. To prevent data overlap, suitable guardbands are positioned between each of the ranges within the frame to uniquely identify the synchronizing pulses, thereby avoiding unidentified and erroneous data transmission.

Figure 5:
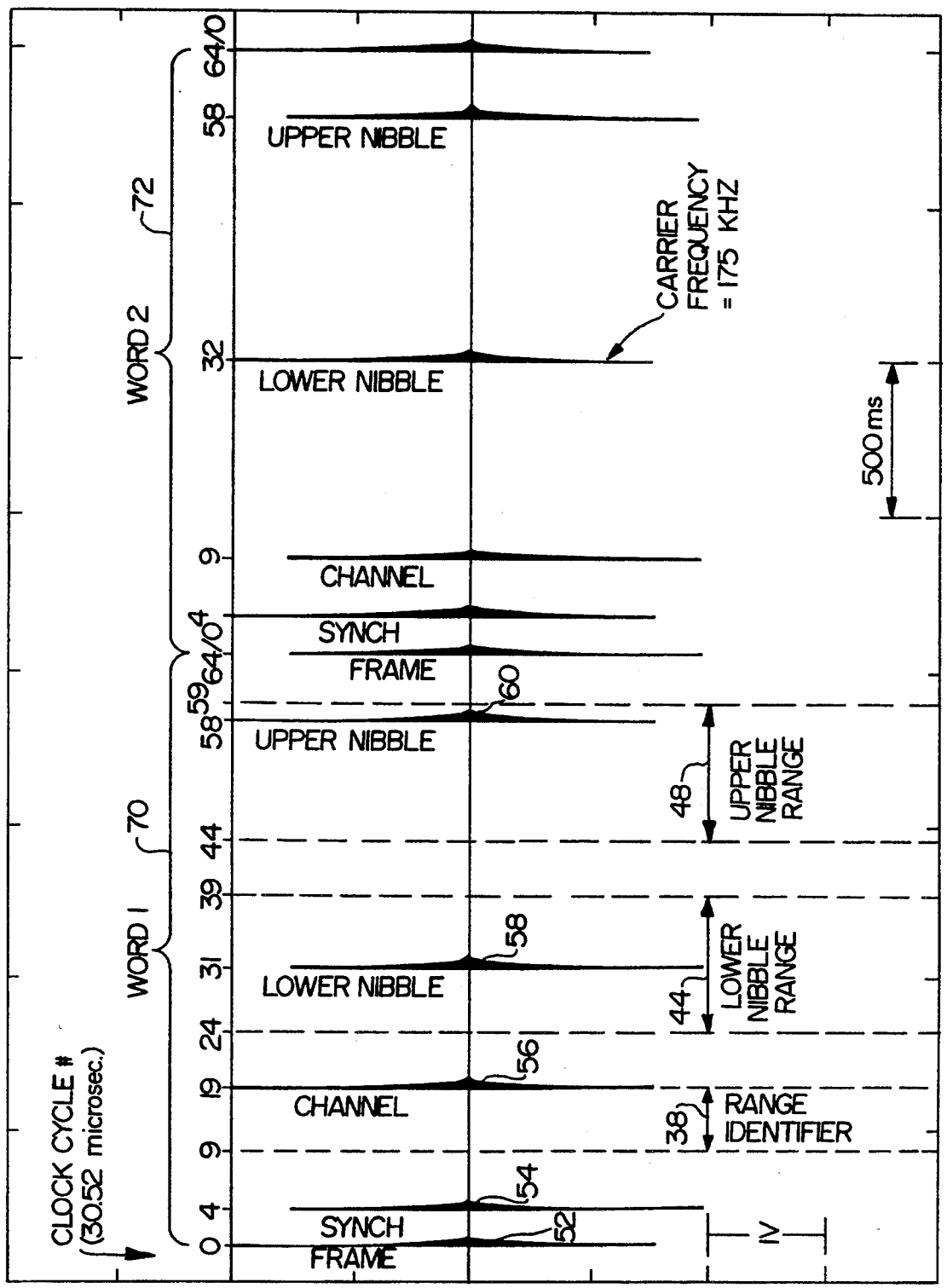
FIG. 5 is a view of the actual transmission pattern of two frames of the telemetry format.

FIG. 5 is a diagram of two frames of RF uplink 26, wherein a first frame corresponds to Word 1 shown at 70, and a second frame corresponds to Word 2 shown at 72. A count of clock cycles is indicated along an upper horizontal axis of this diagram for each frame. Each basic clock cycle has a duration of 30.52 microseconds. The first frame at 70 is initiated by an RF pulse 52. A synchronizing RF pulse 54 is shown uniquely identified as precisely four clock cycles later. Because the guardbands are all greater than four clock cycles, no combination of a frame identifier and data can appear as a synchronizing pulse. Synchronizing pulse 54 is used to provide frame synchronization between the transmitter (i.e., implantable pulse generator 10) and the receiver (i.e., programmer 20).

An identifier RF pulse 56 is located within identifier range 38, which range is defined as nine to nineteen basic clock cycles from the beginning of frame 70. In Word 1, for example, identifier pulse 56 is located at clock cycle nineteen. This identifies the frame as a particular type of date transfer, namely, "Sense Threshold" as indicated in Table 1 below.

TABLE 1

| Position | Identification |
| --- | --- |
| 9 | Memory |
| 10 | Idle |
| 11 | EGM-1 |
| 12 | Markers |
| 13 | Peak Sense |
| 14 | Pressure Waveform |
| 15 | Peak dp/dt |
| 16 | Peak Pressure |
| 17 | Delta Capacitor Voltage |
| 18 | Activity Counts |
| 19 | Sense Threshold |

A lower nibble RF pulse 58 is located within lower nibble range 44, which range is defined as twenty-four to thirty-nine basic clock cycles from the beginning of frame 70. In Word 1, for example, lower nibble pulse 58 is located at clock cycle thirty-one, specifying a binary value of seven on a scale of zero to fifteen. An upper nibble RF pulse 60 is located at clock cycle fifty-eight within upper nibble range 48, which range is defined as forty-four to fifty-nine basic clock cycles from the beginning of frame 70, and is demodulated in similar fashion.

Figure 6:
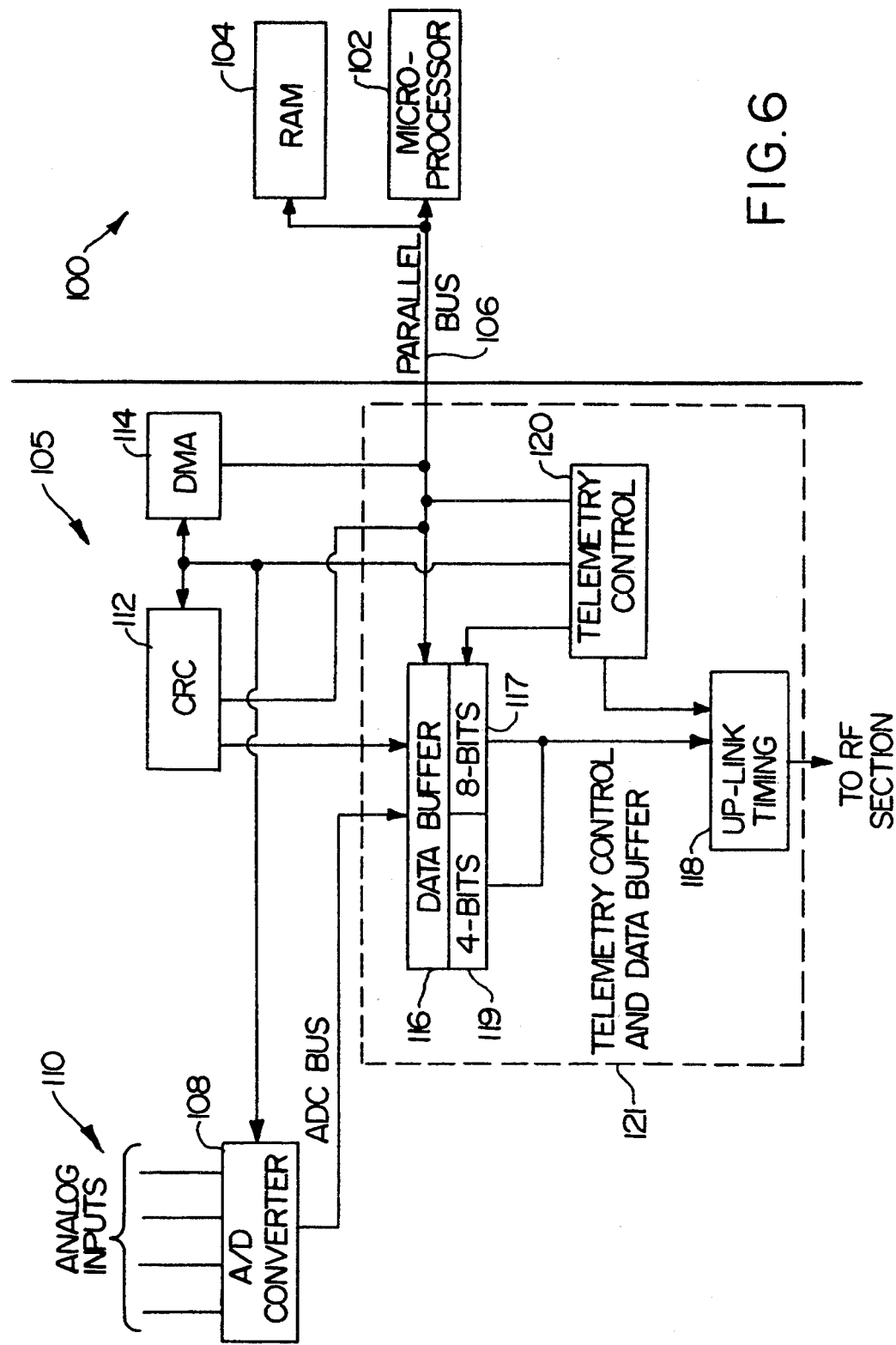
FIG. 6 is a block diagram of a portion of an implantable medical device for implementation of the telemetry format including conversion of analog voltage input to digital signals.

FIG. 6 is a block diagram of that portion of implantable pulse generator be which is associated with formatting and transmission of RF uplink 26. Most of the hardware which embodies the present invention is located on a single substrate, being a custom chip or multiple custom chip device indicated generally by arrows 100 and 105. The remainder is microprocessor-based logic indicated generally by arrow 100, comprising microprocessor 102, random access memory (RAM) 104, and parallel bus 106. The function of microprocessor-based logic 100 is described in further detail below.

Chip 105 has an analog-to-digital (A/D) converter 108 which receives a number of analog inputs 110 including battery voltage from a multiplexer within the analog-to-digital converter 108. Analog measurement of battery voltage can be accomplished by methods and apparatus that are well known to those skilled in the art. A/D converter 108 permits data to be transferred via RF uplink 26 to be digitized as necessary, so that all data is transmitted in a standardized digital form.

Circuitry (CRC) for generating and analyzing the cyclic redundancy code used to forward error detect telemetry data transmitted over RF uplink 26 is indicated at 112. In the preferred embodiment, it is also used for data received by implantable pulse generator 10 via a downlink (not shown). Circuitry (DMA) for providing direct memory access to RAM 104 is indicated at 114, thus permitting multiple byte transfers without constant management by microprocessor 102.

Key hardware used to implement RF uplink 26 comprises telemetry control and data buffer circuitry indicated generally within dashed lines at 121, which circuitry includes data buffer 116 and telemetry control 120, and uplink timing circuitry 118. Data buffer 116 includes storage for twelve bits of data. This storage is partitioned into a four-bit section 119 for storage of the frame identifier code, and an eight-bit section 117 for storage of the lower nibble and upper nibble of a frame. Date buffer 116 thus stores all of the variables for one complete frame. Data buffer 116 is used to stage the variables for the frame data which may be received from RAM 104, A/D converter 108, CRC 112, or elsewhere along parallel bus 106.

Telemetry control 120 consists primarily of a telemetry status register. This register stores the telemetry commands and status as loaded by microprocessor 102. The contents of the register are thus used to gate the data at the proper time of the defined protocol.

Up-link timing 118 encodes the twelve bits of data stored in data buffer 116 to produce a set of timing signals which key bursts of RF energy at the appropriate times to pulse position modulate the 175 kilohertz carrier. Up-link timing 118 also keys bursts of RF energy at the fixed positions within the frame corresponding to the frame-initiating pulse and the synchronizing pulse.

Figure 7:
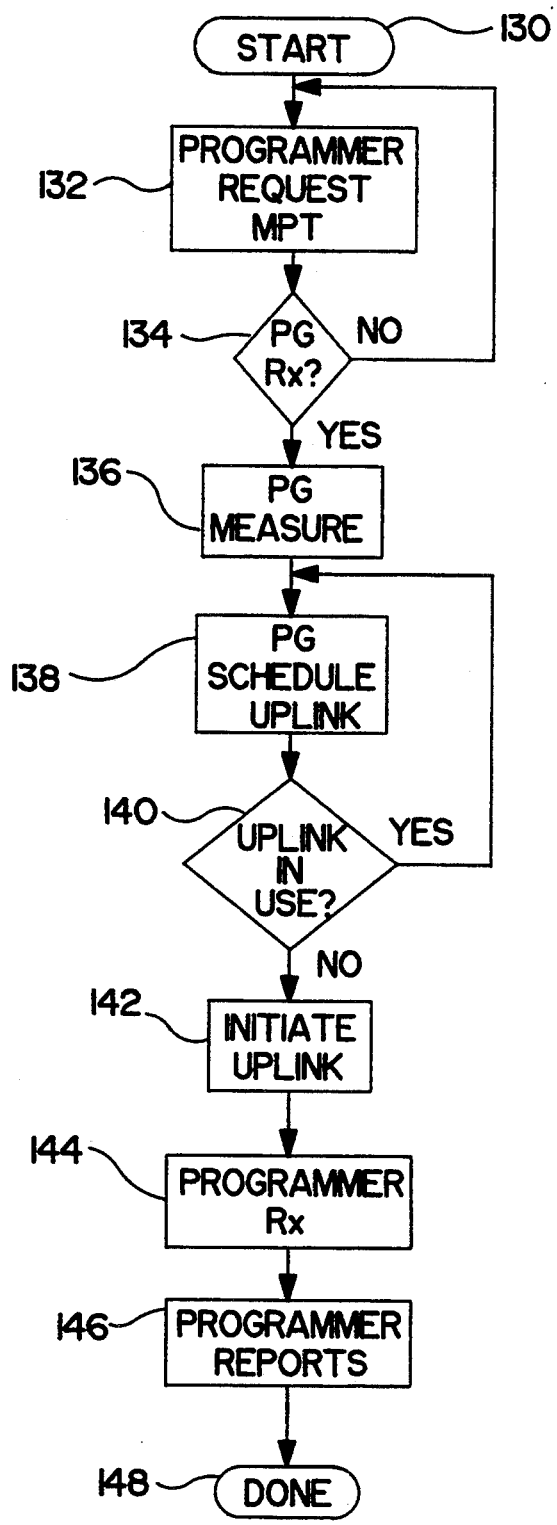
FIG. 7 is a simplified flowchart showing the basic function of software to perform the telemetry uplink operation of the telemetry format.

FIG. 7 is a basic flowchart showing the overall function of the microprocessor-based logic 100 and external programmer in conjunction with this invention. Software associated with RF uplink 26 is started at element 130, by a request from the use of the programmer via a keystroke or light pen entry.

At element 132 the programmer 20 requests measured parameter telemetry (MPT) via standard downlink telemetry as known to those skilled in the art. At element 134, the implantable pulse generator 10 (PG) tests for a correct downlink request. At element 136, the PG 10 measures the battery voltage and battery current as will be described later.

PG element 138 schedules the requested transmission via the up-link facilities. This scheduling prioritizes uplink transmission requests. Lower priority is given to continuous real time transfers, such as EGM and battery voltage, whereas higher priority is given to single occurrence transmissions of status information.

After scheduling, PG element 140 determines whether an uplink transmission is currently in progress. If an uplink transmission is in progress, element 140 reschedules the request.

If an uplink transmission is not in progress after scheduling, PG element 142 initiates the uplink transmission by activating telemetry control 120.

After completion of the uplink response at element 144 to the programmer 20 request for MPT, the programmer reports the results to the programmer user via a screen display or a paper copy via a printer (not shown). Exit is via element 148.

While some additional management of the process is required during the transmission, a description of such further details has been omitted, since that would not be necessary for one skilled in the art to fully understand the present invention.

Figure 8:
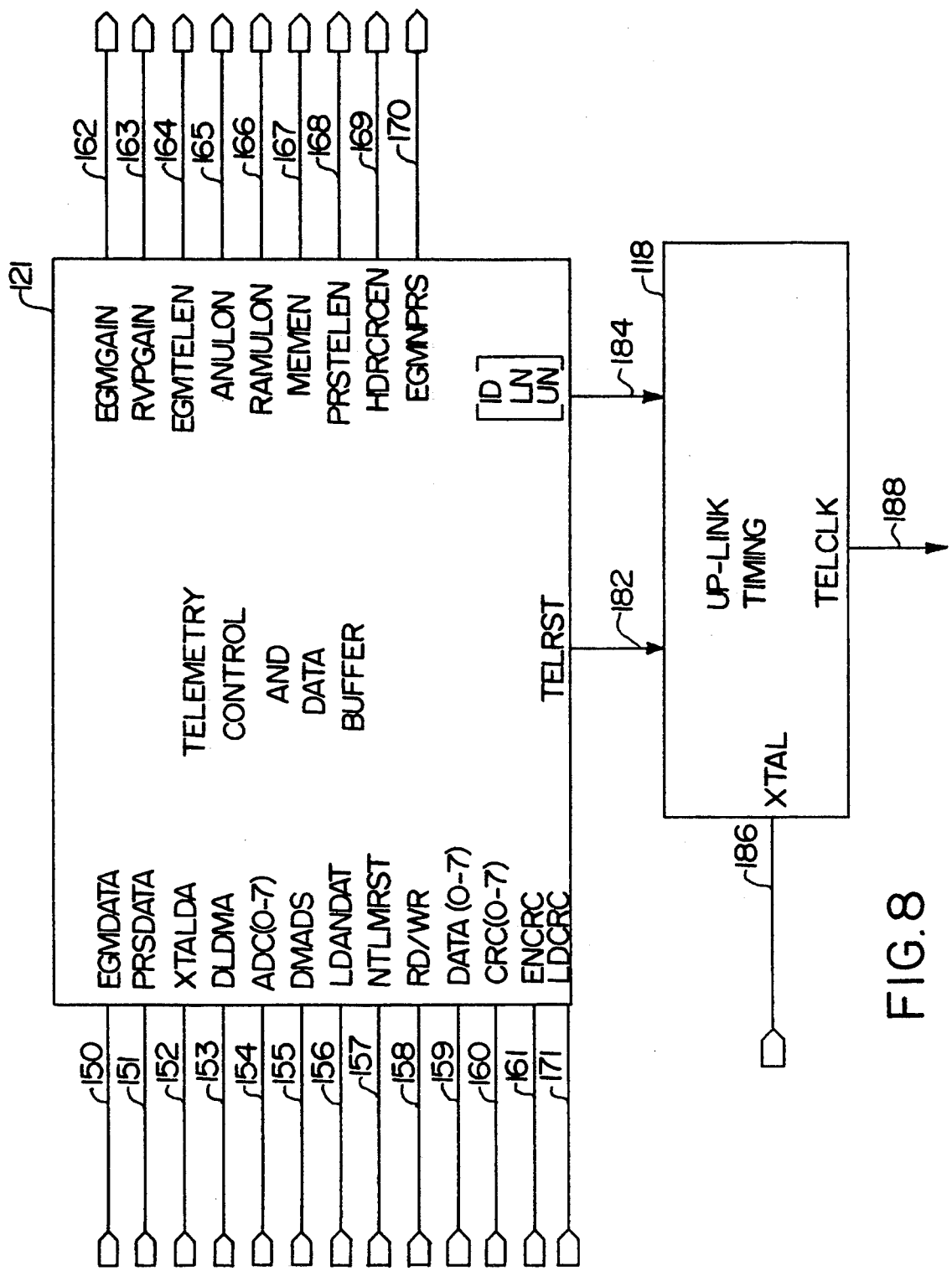
FIG. 8 is a block diagram of the circuitry of the telemetry uplink hardware for implementing the telemetry format.

FIG. 8 is a block diagram showing the major data and control signals of telemetry control and data buffer 121 (which includes data butter 116 and telemetry control 120 shown in FIG. 6), and also of up-link timing 118. A primary function of data buffer 116, as indicated above, is the staging of the twelve variable bits of a given frame which correspond to a four-bit frame identifier ID, and dual-nibble data comprising a four-bit lower nibble LN and a four-bit upper nibble UN. The data is received over an eight-bit, parallel bus 159 and can be from any one of several sources. Control lines EGMDATA at 150, PRSDATA at 151, DLDMA at 153, DMADS at 155, LDANDAT at 156, ENCRC at 161 and LDCRC at 171 specify the source. The output of CRC 112 is presented separately to data buffer 116 as an eight-bit parallel transfer to CRC (0–7) at 160, since those devices are located on the same substrate.

Telemetry control 120 outputs a number of control signals, including EGMGAIN at 162, RVPGAIN at 163, EGMTELEN at 164, ANULON at 165, RUMULON at 166, MEMEN at 167, PRSTELEN at 168, HDRCRCEN at 169 and EGMNPRS at 170. These control outputs are used to enable and control inputs to data buffer 116. The key outputs of telemetry control and data buffer 121 are TELRST at 182, which resets up-link timing 118 and initiates the beginning of a frame, and a parallel data transfer at 184, which transfers the frame identifier ID, lower nibble LN and upper nibble UN to up-link timing 118.

Up-link timing 118 receives the frame-initiating control signal TELRST at 182 and the parallel data transfer (ID, LN and UN) at 184. A primary function of up-link timing 118 is to key the transmission of 175 kilohertz RF energy at the proper times to indicate start of frame, frame synchronization, frame identifier, lower nibble and upper nibble. Timing for this function is provided by the 32.768 kilohertz crystal clock to up-link timing 118 with clock signal XTAL at 186. An output TELCLK is provided at 188 which keys the actual burst of RF carrier at the proper times.

Figure 9:
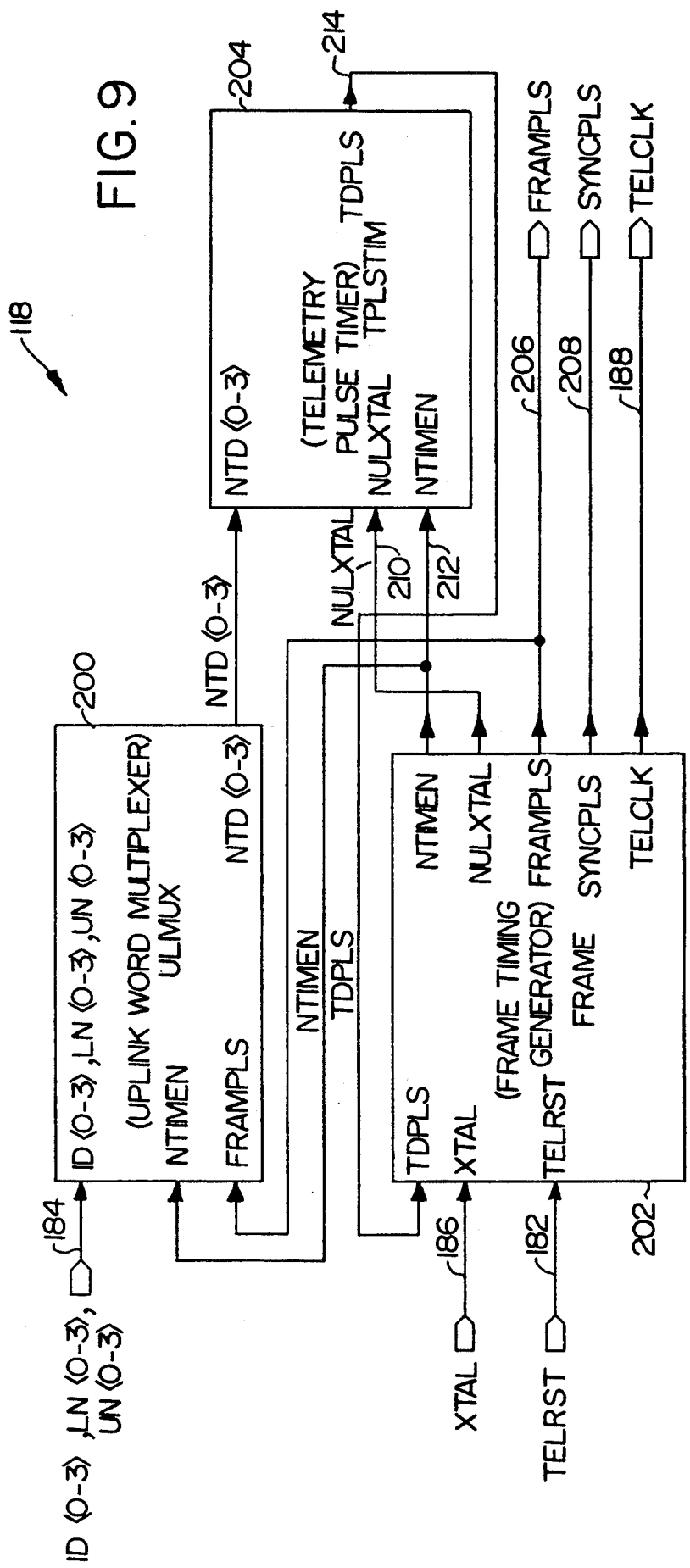
FIG. 9 is a block diagram of the circuitry of the telemetry timing for implementing the telemetry format.

FIG. 9 is a block diagram of up-link timing 118. A frame timing generator 202 provides the desired timing for a frame according to clock input XTAL at 186, in a manner hereinabove explained. Thus, each frame is comprised of sixty-four basic clock cycles. The process is initiated by receipt of the frame-initiating control signal TELRST at 182, which enables uplink when in a low state and disables uplink when in a high state. The initial clock cycle of a frame contains a burst of RF energy which is keyed by control signal TELCLK at 188, which is also used to trigger the start of the data decoding by an uplink word multiplexer 200.

After the proper four-bit quantity is selected (i.e., frame identifier ID first, lower nibble LN next, and upper nibble UN last), a telemetry pulse timer 204 determines the appropriate timing for a burst to be provided to frame timing generator 202, and a corresponding burst of RF energy is keyed. Each of the four-bit quantities thus results in the keying of a burst of RF energy at the appropriate time within each frame.

Figure 10:
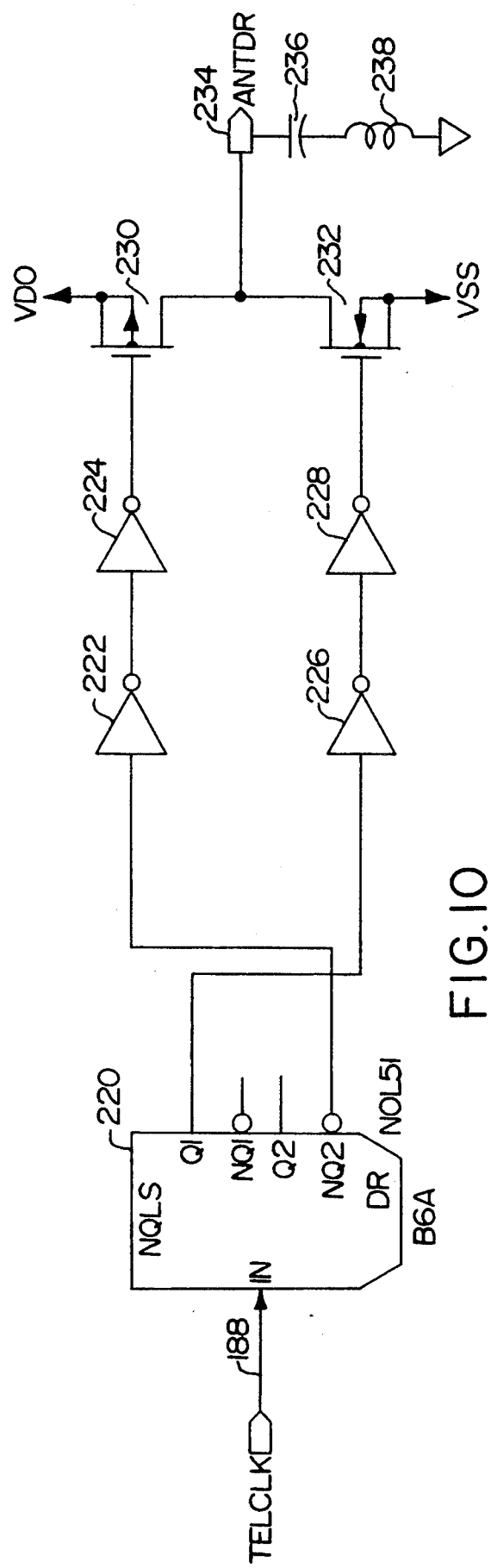
FIG. 10 is a schematic diagram of the driver circuitry for implementing the telemetry format.

FIG. 10 is a circuit diagram for the drive circuit for generating the RF carrier. A control signal TELCLK at 188 provides the timing information for keying the carrier. A non-overlap generator 220 functions as a delay device to save current by preventing output transistors 230 and 232 from conducting simultaneously. Every transition of control signal TELCLK at 188 causes one transition by non-overlap generator 220. Inverters 222, 224, 226 and 228 are scaled to provide efficient switching with sufficient drive to the gates of transistors 230 and 232. Transistors 230 and 232 drive the signal off of chip 105 to ANTDR at 234 to an antenna circuit. A tuned circuit of discreet components, capacitor 236 and coil 238, are located external to chip 105. Each transition thus causes this tuned circuit to resonate at 175 kilohertz, thereby generating one up-link burst.

Figure 11:
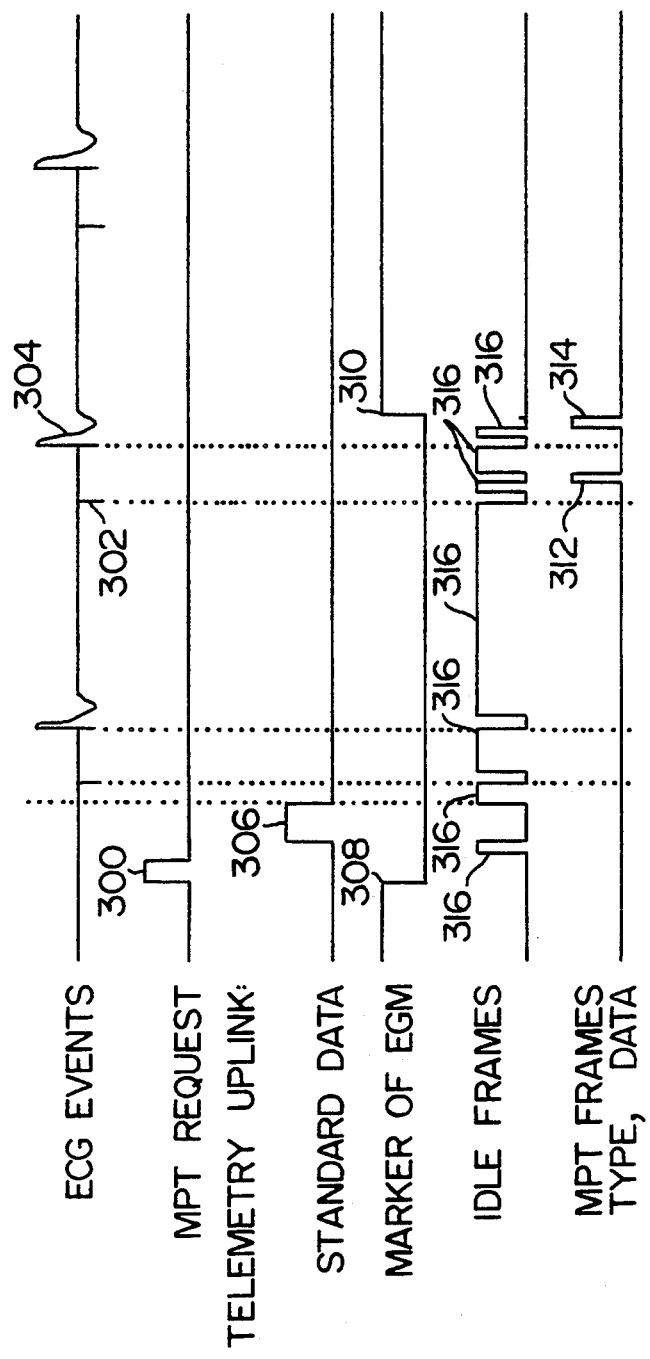
FIG. 11 is a diagram of the measured parameter request sequences for a dual chambered pacemaker.
Figure 12:
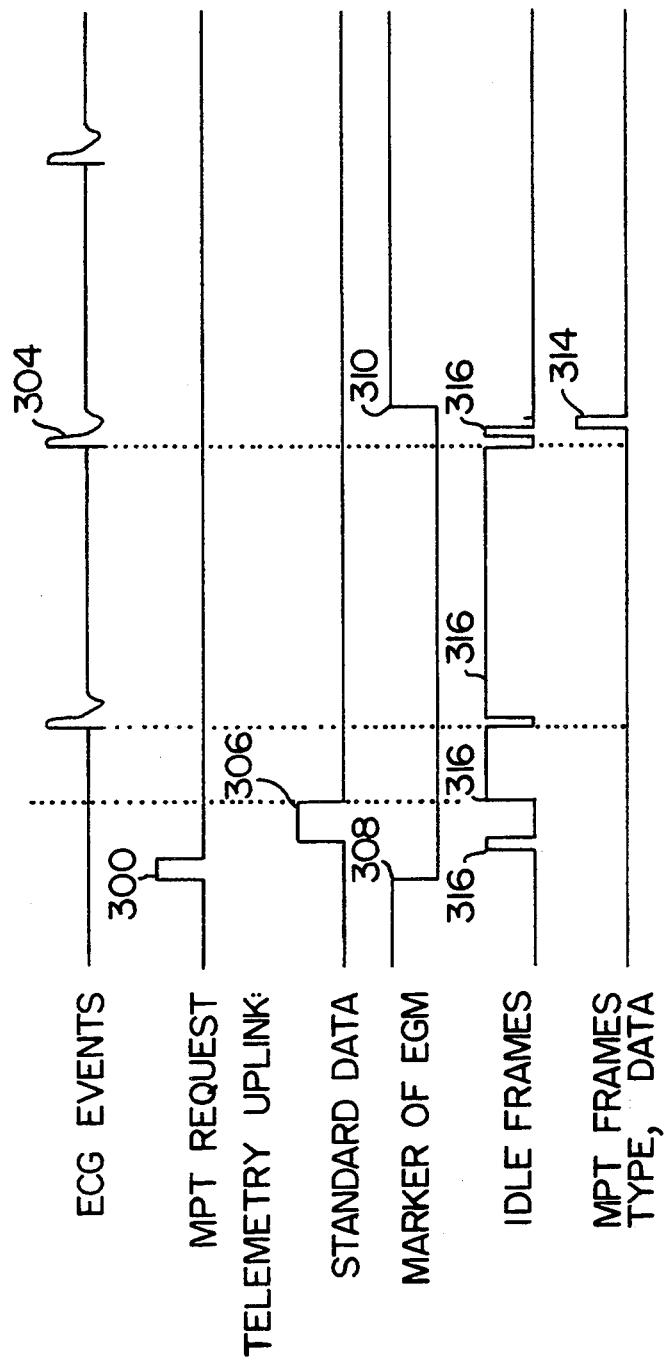
FIG. 12 is a diagram of the measured parameter request sequences for a single chamber pacemaker.

FIG. 11 and FIG. 12 show the measured parameter telemetry request sequences for dual chamber and single chamber pacemakers respectively. The following description relates to both figures. A programmer request 300 for Measured Parameter Telemetry (MPT) initiates the measurement of selected pacemaker data (i.e., battery voltage, output pulse width, output pulse amplitude, lead current, or battery current). In this preferred embodiment, the battery voltage value is measured at the second ventricular event 304 following a MPT request in VVI/VVIR modes, at the second atrial event 302 following a MPT request in AAI/AAIR modes, or at the second atrial event 302 and ventricular event 304 following a MPT request in DDD/DDDR modes. Standard uplink data 306 (e.g., model ID, status and parameter data) is uplinked immediately upon receipt of the MPT request with an pacemaker status bit value a data "1" until completion of the measurement and uplink process (this is used to indicate a measurement in process). Upon initiation of the downlink MPT request transmission 300, the markers or EGM transmission 308 in process will be terminated until the measurement and uplink process is completed at 310. MPT idle frames are transmitted at 316 during the period of time the marker or EGM transmission is off (308 to 310) except for the uplink transmission of the measured data (at 312 or 314). Measured battery voltage data is transmitted via an 8 bit word (B0-B7) preceded by a type identifier: (A0-A7)

|  | A0 | A1 | A2 | A3 | A4 | A5 | A6 | A7 |
|---|---|---|---|---|---|---|---|---|
| Atrial | 0 | 0 | 0 | 0 | 0 | 0 | 0 | 0 |
| Ventricular | 0 | 1 | 0 | 0 | 0 | 0 | 0 | 0 |

Both type identifiers and data are transmitted twice and compared at the programmer for simple error detection. The equation for battery voltage (BV) is as follows:

$$BV = \frac{V\,Ref}{Gain}\left[\frac{B7}{2} + \frac{B6}{4} + \frac{B5}{8} + \frac{B4}{16} + \frac{B3}{32} + \frac{B2}{64} + \frac{B1}{125} + \frac{B0}{256} + \frac{1}{512}\right]$$

where
V Ref = 1.2 volts
Gain = 0.375
(Both constant values stored in programmer)

Battery current telemetry may be determined by any of several methods as is known in the art. For example, U.S. Pat. No. 4,556,061 shows a method for measuring battery current via sampling the voltage across a small resistor connected between the battery and pacemaker circuit.

Upon receipt of both the battery voltage and battery current uplink data, the programmer may report expected time to end of service by comparing the battery voltage to the voltage value shown in FIG. 2. A percentage capacity remaining is determined and with the uplinked battery current data value, the time to recommended replacement (Time RR) may be calculated:

$$Time_{RR} = \frac{AH \times Remaining\ Capacity\ \%}{Battery\ Current}$$

Where AH = Battery Amps Hour Capacity

In a preferred embodiment, the data in FIG. 2 is stored in a lookup table in the programmer 20. Alternatively, the battery characteristic data in FIG. 2 may be realized by a polynomial allowing the programmer to calculate the expected service life directly. The programmer may then report to the user the percent battery capacity used, the percent battery capacity remaining and the expected time to recommend replacement.

While the invention has been described above in connection with the particular embodiments and examples, one skilled in the art will appreciate that the invention is not necessarily so limited. It will thus be understood that numerous other embodiments, examples, uses and modifications of and departures from the teaching disclosed may be made as to various other systems for obtaining end-of-service information for an implantable medical device, without departing from the scope of the present invention as claimed herein.

We claim:

1. A medical device having battery end-of-service indication comprising:
   (a) an implantable housing;
   (b) a medical device within said implantable housing,
   (c) a cathode-limited electrochemical cell having an active metal anode and a manganese dioxide cathode within the housing;
   (d) analog voltage measurement means within the housing for measuring a voltage of the electrochemical cell;
   (e) analog-to-digital conversion means within the housing for converting the measured analog voltage into a digital signal; and
   (f) telemetry means within the housing for telemetry of the digital signal.

2. A medical device according to claim 1 wherein the active metal anode is lithium.

3. A medical device according to claim 2 wherein a capacity ratio of lithium anode to manganese dioxide in the cathode limited electrochemical cell is in a range of about 1.0 to about 1.5.

4. A medical device according to claim 1 wherein telemetry of the digital signal is accomplished by pulse position modulation.

5. A medical device according to claim 1 wherein telemetry of the digital signal includes means for multiple voltage data transmission and means for error detection.

6. A method for determining battery end-of-service for implantable medical device comprising:
   (a) providing a cathode limited electrochemical cell having an active metal anode and a manganese dioxide cathode in an implantable medical device;
   (b) measuring a voltage of the cathode limited electrochemical cell in analog form;
   (c) converting the analog voltage measurement into a digital signal; and
   (d) transmitting the digital signal from the implantable medical device.

7. A method according to claim 6 wherein the step of providing an electrochemical cell includes the step of providing a lithium anode.

8. A method according to claim 7 wherein the step of providing an electrochemical cell includes the step of providing lithium anode and manganese dioxide cathode in the electrochemical cell in a capacity ratio of lithium to manganese dioxide in the cell in a range of about 1.0 to about 1.5.

9. A method according to claim 6 wherein the step of transmitting of the digital signal is accomplished by pulse position modulation.

10. A method according to claim 6 wherein the step of transmitting the digital signal includes transmitting the digital signal at least twice with error detection comparison of the transmitted digital signals.

* * * * *